United States Patent
Green et al.

(10) Patent No.: US 8,190,481 B2
(45) Date of Patent: May 29, 2012

(54) ANONYMOUS PHARMACY ORDER PROCESSING

(75) Inventors: Bonnie Determan Green, St. Louis Park, MN (US); Jo Aldrich, Coon Rapids, MN (US); Kevin Anders Johanson, Lakeville, MN (US); Debra Viramontes, St. Paul, MN (US); Courtney Cole, St. Michael, MN (US); Jayachandran Chandrashekaran, Shakopee, MN (US); Michael Scott Rutkowski, Woodbury, MN (US)

(73) Assignee: Target Brands, Inc., Minneapolis, MN (US)

( * ) Notice: Subject to any disclaimer, the term of this patent is extended or adjusted under 35 U.S.C. 154(b) by 244 days.

(21) Appl. No.: 12/638,335

(22) Filed: Dec. 15, 2009

(65) Prior Publication Data

US 2011/0145080 A1    Jun. 16, 2011

(51) Int. Cl.
*G06G 1/12* (2006.01)

(52) U.S. Cl. ............ 705/21; 705/22; 705/14.65; 705/16; 235/375; 235/385; 700/22

(58) Field of Classification Search .................... 705/21; 235/375, 385

See application file for complete search history.

(56) References Cited

U.S. PATENT DOCUMENTS

| | | | |
|---|---|---|---|
| 5,597,995 A * | 1/1997 | Williams et al. ............ 235/375 |
| 6,522,945 B2 | 2/2003 | Sleep et al. |
| 7,006,214 B2 | 2/2006 | Rzasa et al. |
| 7,343,224 B2 | 3/2008 | DiGianfilippo et al. |
| 7,630,908 B1 * | 12/2009 | Amrien et al. ................ 705/3 |
| 2004/0088187 A1 | 5/2004 | Chudy et al. |
| 2005/0108046 A1 | 5/2005 | Craft |
| 2005/0283259 A1 * | 12/2005 | Wolpow ......................... 700/22 |
| 2007/0088596 A1 | 4/2007 | Berkelhamer et al. |
| 2007/0124170 A1 | 5/2007 | Cabell et al. |
| 2008/0306769 A1 | 12/2008 | Roberts et al. |
| 2009/0076850 A1 | 3/2009 | Hansell et al. |

OTHER PUBLICATIONS

Cam32 Pharmacy Point of Sales Software [Online}, dated Sep. 18, 2009, Retrieved Sep. 18, 2009 from http://www.camcommerce.com/shops/CAM32PharmacyPointofSaleSoftware.aspx.

VIP Point of Sales Software {Online], date unknown, Retrieved on Dec. 7, 2009 from www.vip-pharmacy.com/VIP_Products_PointofSale.html.

* cited by examiner

*Primary Examiner* — Vanel Frenel
(74) *Attorney, Agent, or Firm* — Nixon & Vanderhye P.C.

(57) ABSTRACT

In an illustrative implementation, an anonymous pharmacy order processing system includes means for protecting downstream systems from exposure to confidential identity information, thereby protecting a customer's privacy. In a preferred embodiment, a pharmacy system can generate a generic identifier corresponding to a prescription. The pharmacy system optionally sends the generic identifier to a point of sale system. The point of sale system receives the generic identifier and sends a sale confirmation to the pharmacy system. Furthermore, the point of sale system sends transaction information, including the generic identifier to a transaction system. The pharmacy system receives the sale confirmation and sends a correction transaction with an actual item identifier to the transaction system. The transaction system propagates sales including the generic item identifier to an audit system. Furthermore, the transaction system sends an inventory correction including the actual item identifier to an inventory system.

20 Claims, 5 Drawing Sheets

ANONYMOUS PHARMACY ORDER PROCESSING

TECHNICAL FIELD

This document relates to computer-implemented pharmacy transactions.

BACKGROUND

A doctor or other health care provider can write a prescription for medication. Oftentimes, the prescription is written on a special prescription pad with instructions that the doctor signs. The prescription is taken to a pharmacy for review and filling and a pharmacist reviews the prescription for interactions and side effects. The pharmacist and/or a technician fills and labels the prescription and performs a double check to make sure there are no errors before the patient obtains the medication.

Electronic prescriptions can be accessed and updated over a network. For example, a prescription can be sent from a hospital directly to a patient's pharmacy without relying on a handwritten prescription, thus preventing loss or theft. The patient can then obtain the prescribed medications from the pharmacy. Automated systems are sometimes used to alert doctors and pharmacists to potential interactions and side effects. Some computer systems containing patient information can check for allergies and appropriate dosing.

Computerized inventory tracking systems are also used in pharmacies. The systems can keep count of medications for accurate bookkeeping, ease of reordering, and to limit access to narcotics and other controlled drugs. When a medication is taken from inventory, for example, to fill a prescription, the count of the medication is decremented in the inventory. Computerized inventory tracking systems can be used to provide data to reorder medications. For example, a pharmacy buyer prints a list of medications that have low inventory and orders more. Computerized inventory systems can be used to provide inventory data for analysis, for example, to track usage trends.

Point of sale systems are used to manage transactions in retail environments, such as a retail pharmacy. A cashier can sell a filled prescription to a customer and use the point of sale system to accept payments such as cash or credit cards. The point of sale system can calculate sales tax and add the appropriate amount to the cost of the medication. Some point of sale systems include bar code scanners, which a cashier can use to check out items quickly and efficiently.

Transaction clearing systems are used to manage transactions from point of sale systems. Some transaction clearing systems reconcile payments with financial institutions and reconcile inventory with an inventory system. For example, a customer has a prescription filled at a pharmacy and purchases the medication at a point of sale system. The transaction clearing system can clear the purchase with an automated clearing house and can update inventory.

SUMMARY

In an illustrative implementation, an anonymous pharmacy order processing system includes means for protecting downstream systems from exposure to confidential identity information, thereby protecting a customer's privacy. In a preferred embodiment, a pharmacy system can generate a generic identifier corresponding to a prescription. The pharmacy system optionally sends the generic identifier to a point of sale system. The point of sale system may receive the generic identifier and sends a sale confirmation to the pharmacy system. Furthermore, the point of sale system may send transaction information, including the generic identifier to a transaction system. The pharmacy system may receive the sale confirmation and send a correction transaction with an actual item identifier to the transaction system. The transaction system may propagate sales including the generic item identifier to an audit system. Furthermore, the transaction system may send an inventory correction including the actual item identifier to an inventory system.

Furthering that example, use of a generic identifier for a prescription may aid in preventing the point of sale system and other systems, such as the audit system or the inventory system, from tying confidential information to a prescription. In certain embodiments, when the transaction system sends an inventory correction to the inventory system, the inventory correction does not include information tying the particular item or items to a transaction. In another example, when the transaction system sends sales information to the audit system, the generic identifier is used rather than the actual identifier, thus preventing the audit system from tying the sales information to an actual identifier.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION OF ILLUSTRATIVE IMPLEMENTATIONS

Figure 1:
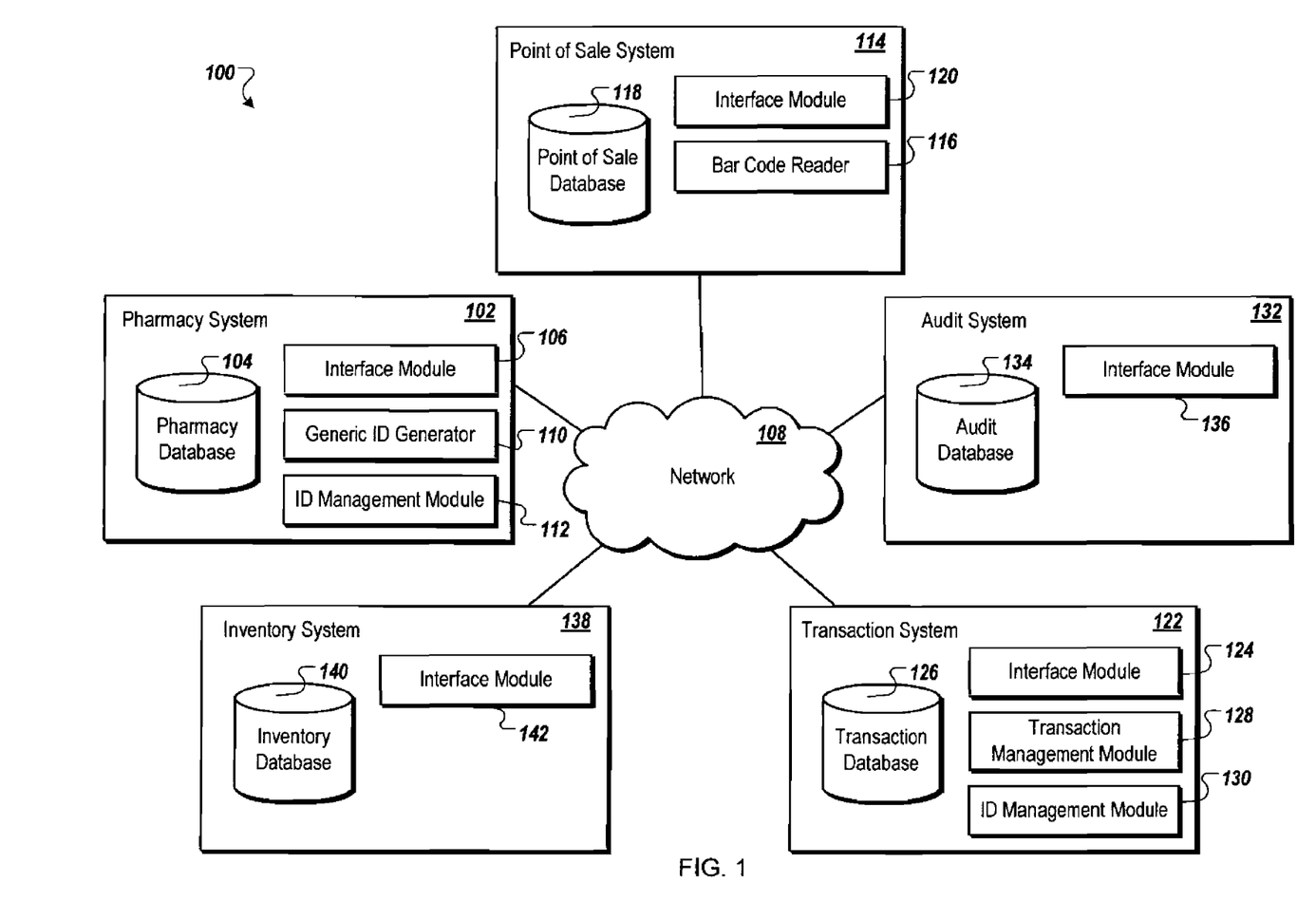
FIG. 1 depicts an example system that can be used for content distribution.

FIG. 1 depicts an example system 100 that can be used for pharmacy transaction clearing. The system 100 includes a pharmacy system 102. The pharmacy system includes means for inputting, updating, and accessing pharmacy data (not shown). In some implementations, the pharmacy system is a prescription system. For example, pharmacy employees (e.g., pharmacists and/or technicians) use a pharmacy system to access, verify, and update prescriptions. In a retail environment, the pharmacy system 102 is used in a similar way, including accessing or downloading electronic prescriptions.

The pharmacy system 102 includes a pharmacy database 104. For example, the database includes one or more relational databases, such as an SQL database. The pharmacy database 104 includes information such as patient, drug, and prescription information, to name just a few examples. The pharmacy database optionally includes information that is regulated by the Health Insurance Portability and Accountability Act (HIPAA). A hospital or retailer might wish to take steps to ensure the privacy of HIPAA regulated information, such as having the information reside on a system in which the flow of information in or out of is controlled to limit exposure of the information unnecessarily. For example, individuals may only want their prescription information available to certain care providers, such as a doctor and/or pharmacist. Accordingly, the individual may not want other people, such as the cashier ringing up a transaction, to have access to that prescription information. In that example, the information is restricted to certain systems, such as the pharmacy system 102, and outgoing information is tailored to provide reasonable privacy for the individuals.

The pharmacy system 102 includes an interface module 106. The interface module 106 includes software and/or hardware to facilitate communications with other systems over a network 108. In some implementations, the interface module 106 downloads information from systems or databases external to the pharmacy system 102. For example, the interface module 106 encodes messages into data packets, and the network can route the data packets appropriately. Other systems include a module that provides a similar or identical function to the interface module 106. In some implementations, the pharmacy system 102 is connected to another network to retrieve information.

The pharmacy system 102 includes a generic ID generator 110. For example, a generic ID includes a sequence of characters (e.g. alphanumeric characters or symbols) and can be encoded into a machine readable format, such as an image or a bar code. In some implementations, the generic ID can be representative of information stored within the pharmacy database 104, such as a prescription. The generic ID generator 110 includes or is connected to a label printer. For example, a pharmacist preparing medications optionally prints a label such that a different person selling the medication to a customer (e.g. a cashier) cannot determine the medications from the label. In that example, the label includes information necessary to price the item correctly, and to ensure the correct item is given to the correct customer. A label can include any or all of a patient name, price, or bar code, to name just a few examples.

The pharmacy system 102 includes an ID management module 112. The ID management module keeps track of IDs generated by the generic ID generator 110. The ID management module 112 updates the pharmacy database 104 or another database with an ID. For example, when the generic ID generator 110 generates an ID for a prescription that has been filled, the ID management module 112 associates that prescription with the appropriate record or records in the pharmacy database 104. In some implementations, the record in the pharmacy database 104 is marked with an identifier to indicate the associated item or items are pending checkout. The ID management module can check for duplicate IDs or other conflicts, and take appropriate action. For example, the generic ID generator 110 waits for confirmation from the ID management module 112 before authorizing a label to be printed. The ID management module also keeps track of what generic IDs have been issued so that when a labeled item is sold to a customer, the pharmacy system 102 can reconcile the transaction and notify other systems about the completed sale. The generic ID is generated for and/or associated with a single medication, or for a group of medications. For example, a bag is labeled with a generic ID, but contain multiple items from the same or a different prescription.

The system 100 includes a point of sale system 114 to facilitate a sale or other retail transaction with a customer. In some implementations, the point of sale system is a retail system. For example, the point of sale system includes a checkout terminal and associated hardware and software for selling medications or other products to a customer. In some implementations, the point of sale system includes additional hardware and software for completing a transaction with various cards (e.g. credit, debit, gift), checks, electronic payments, coupons, discounts, and/or rewards cards, to name a few examples. The point of sale system 114 includes a bar code reader 116. In some implementations, the bar code reader can be used to read a bar code generated by the generic ID generator 110. For example, a cashier uses the point of sale system 114 and the included bar code reader 116 to scan a bar code on a medication container. In some implementations, the bar code reader is capable of reading other machine generated identifiers or information.

The point of sale system includes a point of sale database 118. For example, the database includes one or more relational databases, such as an SQL database. The point of sale database contains information about pending or completed sales. For example, the point of sale database stores an ID generated by the generic ID generator 110. The point of sale database optionally includes other information, such as information related to computing sales tax or information to help ensure that the correct medication container gets to the correct customer, for example. The point of sale database also optionally includes information about whether a sale has been completed for an item labeled with an ID generated by the generic ID generator 110.

The point of sale system includes an interface module 120, similar to the interface module 106, for facilitating communications over the network 108. For example, the pharmacy system 102 electronically send IDs generated by the generic ID generator and/or other associated information to the point of sale system 114. The point of sale system sends IDs and/or other associated information related to a completed transaction to other systems, such as the pharmacy system 102, to name just one example. In some implementations, the point of sale system 114 is connected to another network or networks, such as a secure network for credit and debit card processing. In some implementations, there are multiple point of sale systems, some of which have similar or identical components to the point of sale system 114. For example, the point of sale system includes multiple terminals. In that example, each terminal has a separate bar code reader.

The system 100 includes a transaction system 122 used to manage transactions. In some implementations, the transaction system 122 is an event handler. The transaction system receives updates from various systems, and sends appropriate updates to various systems. For example, the transaction system keeps track of sales made at the point of sale system 114.

The transaction system includes an interface module 124, similar to the interface module 106, for facilitating communications over the network 108. For example, the point of sale system 114 sends sale confirmations to the transaction system 122, and the transaction system acknowledges receipt to the point of sale system and/or other systems. In another example, the pharmacy system 102 also sends sales confirmations to the transaction system 122 with the same or a different ID than the point of sale system 114.

The transaction system 122 includes a transaction database 126. For example, the transaction database includes one or more relational databases, such as an SQL database. The transaction database contains information related to transactions. For example the transaction database contains information relating to sales made at the point of sale system 114, and or sales confirmations from either the point of sale system or the pharmacy system 102.

The transaction system 122 includes a transaction management module 128. The transaction management module manages transactions. For example, the transaction management module updates the transaction database 126 with transactions received from other systems, such as the pharmacy system 102 and/or the point of sale system 114. The transaction management module organizes and handles various aspects of transactions, such as billing and credit card processing, to name two examples.

The transaction system 122 includes an ID management module 130. The ID management module 130 keeps track of IDs sent from other systems, such as the pharmacy system 104 or the point of sale system 114. The ID management module 130 updates the transaction database 126 or another database with the ID or information determined from the ID. The ID management module 130 reconciles two related, but different IDs. For example, the point of sale system 114 sends one ID to the transaction system 122 and the pharmacy system 102 sends a different ID. In that example, the ID management module 130 recognizes the two IDs as either being related or unrelated, and takes appropriate action, such as updating the transaction database 126, and/or databases on other systems. The ID management module 112 performs a similar reconciliation between two related but different IDs.

The system 100 includes an audit system 132. The audit system keeps track of various metrics and statistics related to pharmacy transactions. In some implementations, the audit system is a business analytics or business intelligence system. The audit system 132 includes an audit database 134. For example, the audit database includes one or more relational databases, such as an SQL database. The audit database stores information related to pharmacy transactions from another system, such as the transaction system 122, the point of sale system 114, or the pharmacy system 102. For example, the audit database 134 stores metrics of interest in a corporate environment, such as revenue, expenses, and/or total sales. The audit database stores details of individual transactions, or aggregate data, and is accessed to determine trends, forecast future sales, and/or inventory, to name just a few examples.

The audit system 132 includes an interface module 136, similar to the interface module 106, for facilitating communications over the network 108. For example, the audit database receives information about sales transactions from the transaction system 122.

The system 100 includes an inventory system 138 that keeps track of inventory levels of various medicaments on hand at a retail pharmacy. The inventory system receives updates from other systems, such as the point of sale system 114.

The inventory system 138 includes an inventory database 140 that includes one or more relational databases, such as an SQL database. The inventory database contains information related to inventory, such as current inventory counts for various medications. For example, when an item is sold, the count for that item is updated to reflect the current on-hand inventory.

The inventory system 138 includes an interface module 142, similar to the interface module 106, for facilitating communications over the network 108. For example, the inventory system 138 receives information relating to sales transactions from the transaction system 122. The inventory system stores and/or updates information in the inventory database 140.

Information sent between systems described in the system 100 can be sent directly from one system to another over the network 108. For example, data is addressed to a particular system. In some implementations, information is broadcast to one or more systems on the network. For example, the pharmacy system 102 or the point of sale system 114 sends sales data with a generic ID to one or more additional systems. In some implementations, data is passed along by the various systems. For example, data regarding a sales transaction is sent from the pharmacy system 102 to the inventory system 138 via the transaction system 122. Intermediary systems, such as the transaction system in that example, modify the content of the message to protect the systems from exposure to private data.

In some implementations, the various systems described are implemented on one or more systems. For example, in a retail environment, both the pharmacy system 102 and the inventory system 138 optionally reside on the same server, and share some resources. In that example, additional safeguards are taken to ensure that no private information is transferred between the two systems such as segregation of data, appropriate routing, virtual machines, and/or gatekeepers. In some implementations, systems keeps track of information residing on other systems. As with the previous example, additional safeguards are implemented to protect private information.

Figure 2:
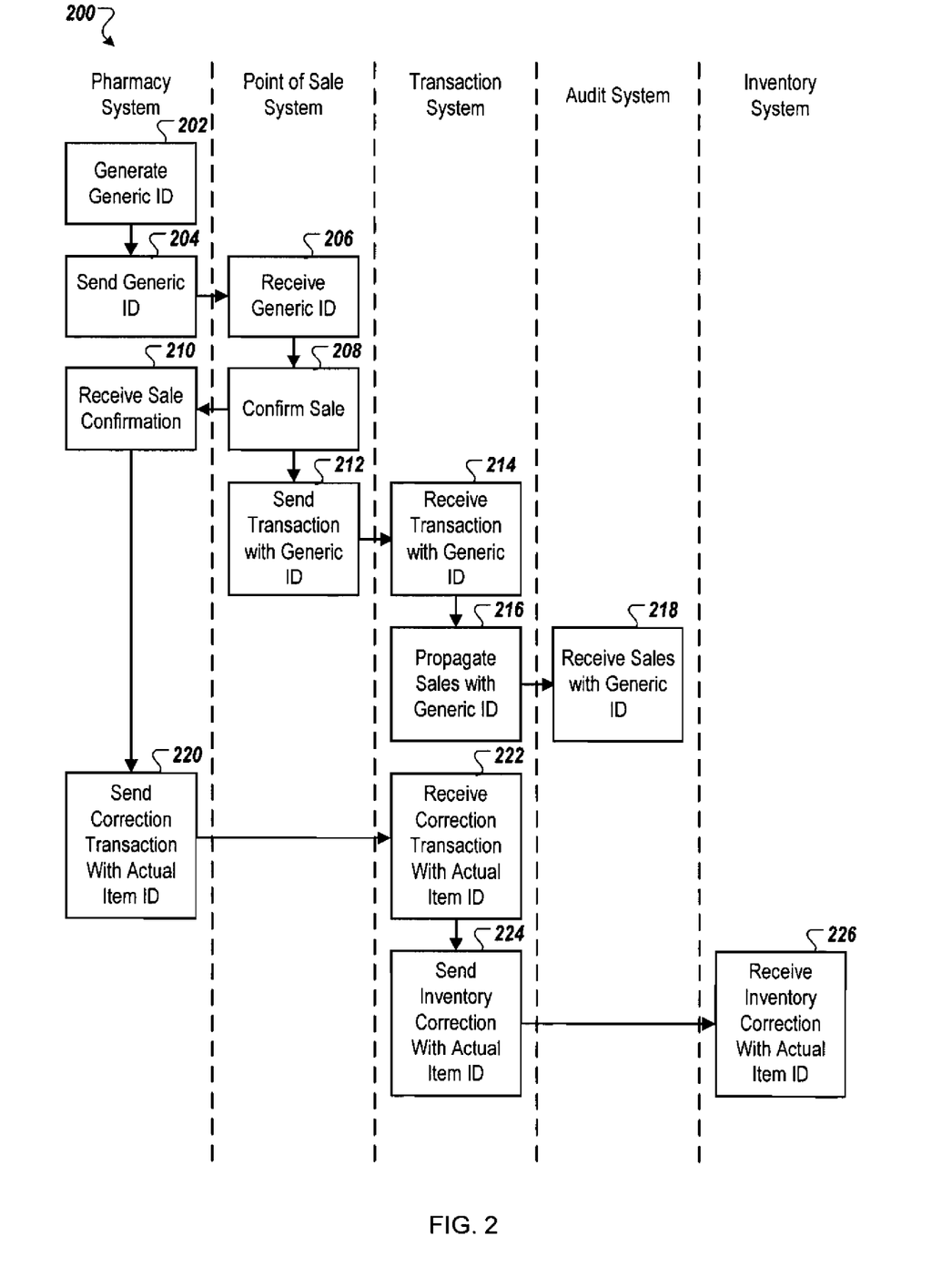
FIG. 2 is a swim lane diagram of an example procedure for pharmacy transaction clearing.

FIG. 2 is a swim lane diagram of an example procedure 200 for pharmacy transaction clearing. The procedure 200 is implemented by the system 100, or another system. In step 202, the pharmacy system 102 generates a generic ID. For example, the generic ID is generated by the generic ID generator 110, and is verified by the ID management module 112. In some implementations, the ID is stored in the pharmacy database 104 and is associated with a prescription. An event triggers generation of the ID. For example, a pharmacist bags a prescription and requests a label so that the medication is sold to a customer. The ID optionally excludes any HIPAA regulated information, for example, the names and dosages of medications contained within a prescription bag.

In step 204, the pharmacy system 102 sends the generic ID to the point of sale system 104. For example, the ID is encoded into a message by the interface module 106 and sent over the network 108 to the point of sale system 114. In some implementations, the generic ID is sent to other systems, such as the inventory system 138.

In step 206, the point of sale system 114 receives the generic ID. The generic ID is received and decoded from a message by the interface module 120 and is written to the point of sale database 118. The generic ID is listed as a pending transaction. Alternatively, the generic ID is received through the bar code reader 116. In some implementations, the generic ID is received more than one time, for example, from both the network 108 and the bar code reader 116.

In step 208, a sale is confirmed by the point of sale system. For example, a cashier scans a medication bag using the bar code reader 116 and sells the medication to the customer. When the sale is confirmed, a confirmation message is sent to another system, such as the pharmacy system 102. For example, the confirmation message includes the generic ID, and other information, such as a customer identity. Furthermore, information about the sale is used to update a database, such as the point of sale database 118. In some implementations, the generic ID does not include HIPAA regulated information, thus the cashier may not use the generic ID to determine the medications. The cashier has access to information necessary to ensure the bag with the correct ID goes to the correct customer. For example, the bag may have the customer's name printed on a label. In another example, the customer may have a ticket corresponding to the generic ID on the package. The cashier may also have access to information necessary to complete the sale, such as the total cost of the items. In some implementations, this information is encoded in the generic ID.

In step 210, the pharmacy system 102 receives a sale confirmation. For example, the pharmacy system receives and decodes a message including the sale confirmation using the interface module 106. The ID management module reconciles the generic ID with an actual ID of the prescription. Information related to the sale confirmation, generic ID, and/or actual ID is written to the pharmacy database 104.

In step 212, the point of sale system 114 sends transaction information including the generic ID to the transaction system 122. For example, the transaction information is encoded into a message by the interface module 106 and sent over the network 108 to the transaction system 122. In some implementations, the transaction information is sent to other systems, such as the inventory system 138 or the audit system 132. In step 214, the transaction system 122 receives the transaction information including the generic ID. For example, the transaction system receives and decodes a message including the transaction information using the interface module 124. The transaction system 122 writes information related to the transaction to the transaction database 126.

In step 216, the transaction system 122 propagates sales including the generic ID to the audit system 132. In one implementation, the transaction system sends sales information for one transaction. In another implementation, the transaction system 122 queues up sales information and sends the information as a group to the audit system. For example, the sales information is encoded into a message by the interface module 124 and sent over the network 108 to the audit system 132. In some implementations, the sales information is sent to other systems.

In step 218, the audit system 132 receives sales information including the generic ID. For example, the audit system receives and decodes a message including the sale confirmation using the interface module 136. The audit system 132 writes information related to the sales information to the audit database 134. In some implementations, the audit system executes an audit of pharmacy sales data without accessing data sufficient to associate a customer with an actual item identifier.

In step 220, the pharmacy system 102 sends a correction transaction with an actual item ID or IDs to the transaction system 122. In some implementations, the actual item ID is a product key. For example, the correction transaction is encoded into a message by the interface module 106 and sent over the network 108 to the transaction system 122. In some implementations, the actual item ID is retrieved from the pharmacy database 104 by the ID management module 112. For example, the receipt of a sale confirmation, such as in step 210, triggers the ID management module 112 to determine what actual ID or IDs are associated with a generated generic ID. In some implementations, the pharmacy sends the generic ID associated with the actual ID or IDs to the transaction system. The correction transaction can indicate items and/or quantities of items.

In step 222, the transaction system 122 receives the correction transaction with the actual item ID. For example, the transaction system receives and decodes a message including the sale confirmation using the interface module 124. The transaction system 122 writes information related to the correction transaction information to the transaction database 126. In some implementations, the transaction system 122 overwrites the associated generic ID entry in the transaction database 126 with the actual ID. In some implementations, the transaction system 122 creates a new entry in the transaction database. For example, if there is no corresponding generic ID or it cannot be determined, the transaction system creates a new entry. In that example, unrecognized transactions are flagged in the transaction database 126, stored in another database, handled by an audit of the various systems, or discarded.

In step 224, the transaction system 122 sends an inventory correction with the actual item ID to the inventory system 138. For example, the correction transaction is encoded into a message by the interface module 124 and sent over the network 108 to the inventory system 138. In some implementations, the inventory correction does not contain customer identity information.

In step 226, the inventory system 138 receives the inventory correction with the actual item ID. For example, the transaction system receives and decodes a message including the inventory correction using the interface module 142. The inventory system 138 writes information related to the correction transaction information to the inventory database 140. For example, the inventory system 138 updates a stock level for items in the inventory database 140 according to the items that were sold to a customer.

In some implementations, the steps described in the procedure 200 are performed in a different order, or take place simultaneously. For example, step 210 takes place at the same time or after step 212. In some implementations, steps performed by systems take place asynchronously. For example, the pharmacy system sends a correction transaction (step 220) before sales information has been propagated to the audit system (steps 216 and 218).

Figure 3:
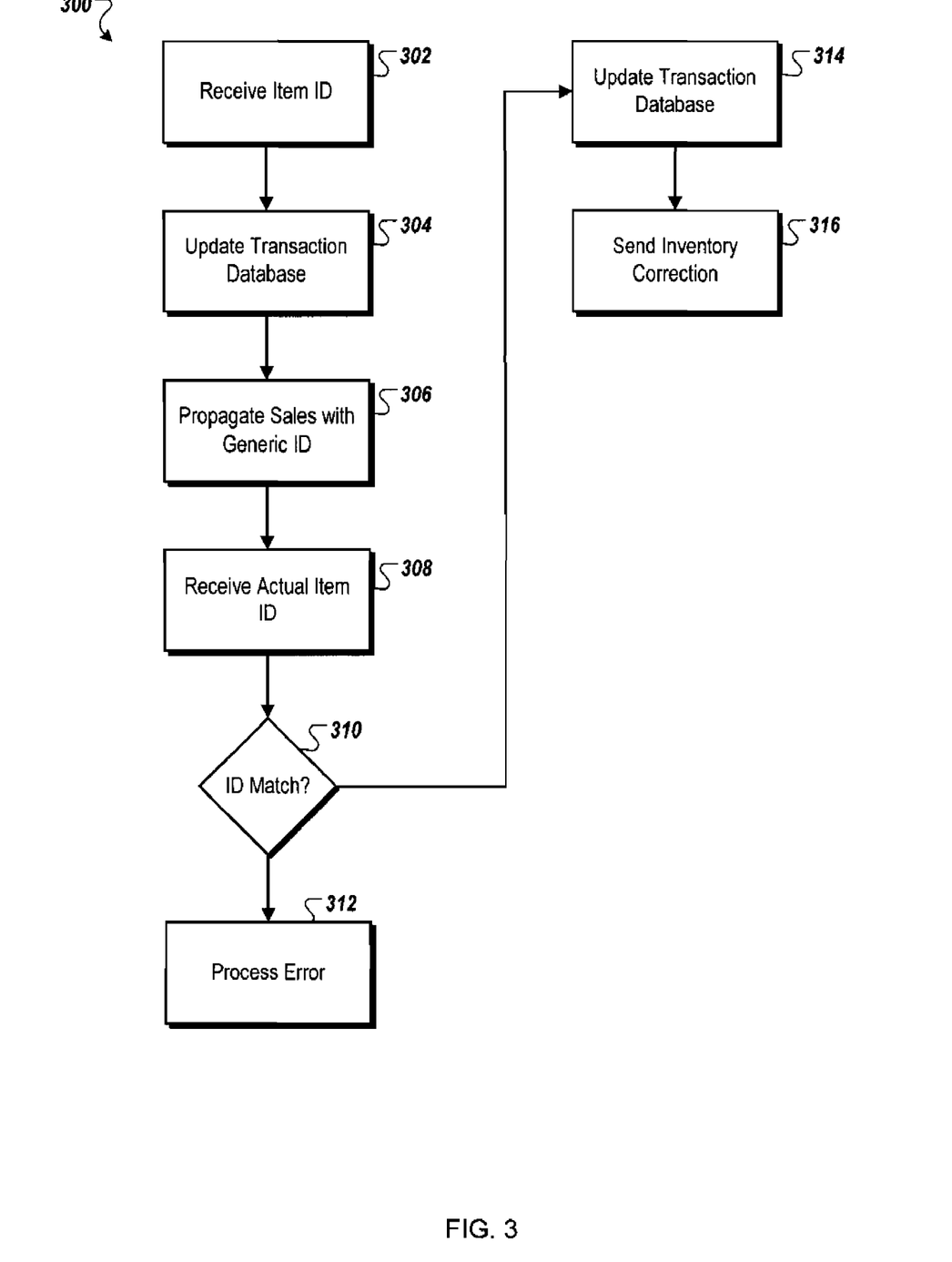
FIG. 3 is a flow chart of an example procedure for clearing pharmacy transactions.

FIG. 3 is a flow chart showing an example procedure 300 for clearing pharmacy transactions. The procedure 300 is performed by the transaction system 122 and will be described as such for clarity. In other implementations, the procedure 300 is performed by another system.

In step 302, the transaction system 122 receives a generic ID. For example, the transaction system receives and decodes a message including the transaction information using the interface module 124.

In step 304, the transaction system 122 updates the transaction database 126. For example, the transaction system 122 stores the generic ID, or information related to the generic ID in the database. For example, the transaction system 122 stores information about the sales transaction, such as the total price of the item or items associated with the generic ID, and/or the time and location the sales transaction took place, to name a few examples. The transaction system segregates records that comprise actual item identifiers from records for the same transaction that comprise generic item identifiers or customer identity information.

In step 306, the transaction system 122 propagates sales with the generic ID. For example, the transaction system sends an update to the audit system 130 via the network 108 and the interface module 124. In some implementations, the sales information that is sent includes similar information to what was stored in the transaction database 126 in step 304 (e.g. price, time location, item or items). In that example, certain information regulated by HIPAA may not be sent to the audit system 132, even if such information is available to the transaction system 122 or other systems.

In step 308, the transaction system 122 receives an actual item ID. For example, the transaction system receives and decodes a message including the transaction information using the interface module 124.

In step 310, the transaction system 122 determines if the actual item ID is related to the generic ID. For example, the ID management module 130 searches for a corresponding generic ID in the transaction database.

If no match is found, the transaction system 122 performs step 312 by processing an error. An error is processed in various ways. For example, the transaction system records the transaction as not being linked to a particular generic ID.

If a match is found in step 310, the transaction system 122 performs step 314 by updating the transaction database 126. For example, the transaction system 122 stores the actual ID, or information related to the actual ID in the database.

In step 316, the transaction system 122 sends an inventory correction to the inventory system 138. For example, the transaction system sends an update to the inventory system 138 via the network 108 and the interface module 124. In some implementations, the inventory correction indicates the quantity and items sold in a transaction, but does not include any HIPAA protected information.

Figure 4A:
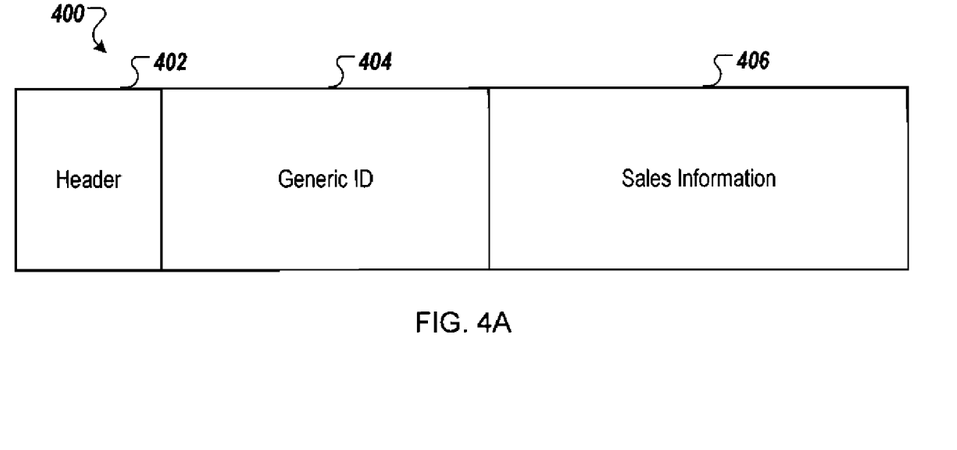
FIGS. 4A through 4C depict example data packets.

FIG. 4A depicts an example data packet 400. The data packet 400 is sent from the point of sale system 114 to the pharmacy system 102. The data packet 400 is created and/or processed by the interface module 120, and transmitted over the network 108. The data packet 400 is received and/or processed by the interface module 106.

The data packet 400 includes a header section 402. The header section includes various information such as a source address, a destination address, routing information, length of message information, and/other information necessary for transmission.

The data packet 400 includes a generic ID section 404. The generic ID section includes the generic ID and other associated information. The data packet 400 includes a sales information section 406. The sales information section includes information from the sale of an item or items associated with the generic ID.

Figure 4B:
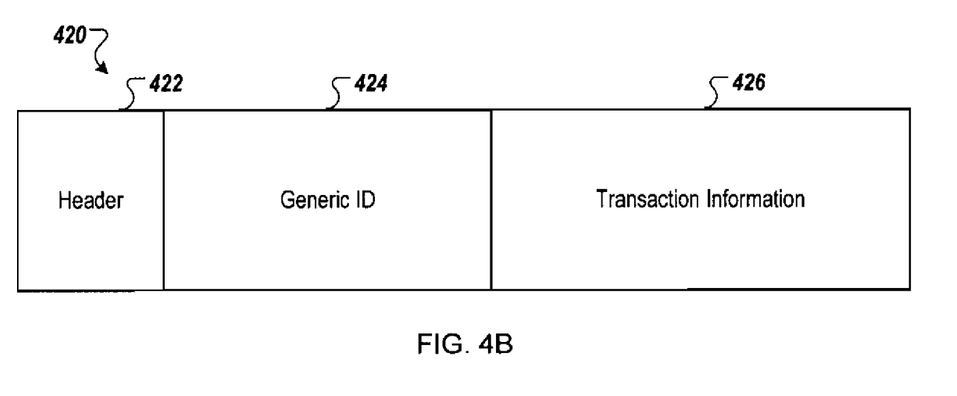

FIG. 4B depicts an example data packet 420. The data packet 420 is sent from the point of sale system 114 to the transaction system 122. The data packet 420 is created and/or processed by the interface module 120, and transmitted over the network 108. The data packet 420 is received and/or processed by the interface module 124. The data packet 420 includes a header section 422, similar or identical to the header section 402. The data packet 420 includes a generic ID section 424, similar or identical to the generic ID section 404.

The data packet 420 includes a transaction information section 426. The transaction information section includes information about the transaction associated with the generic ID. It may contain a time and date stamp, the total price, or the retail location, to name just a few examples.

Figure 4C:
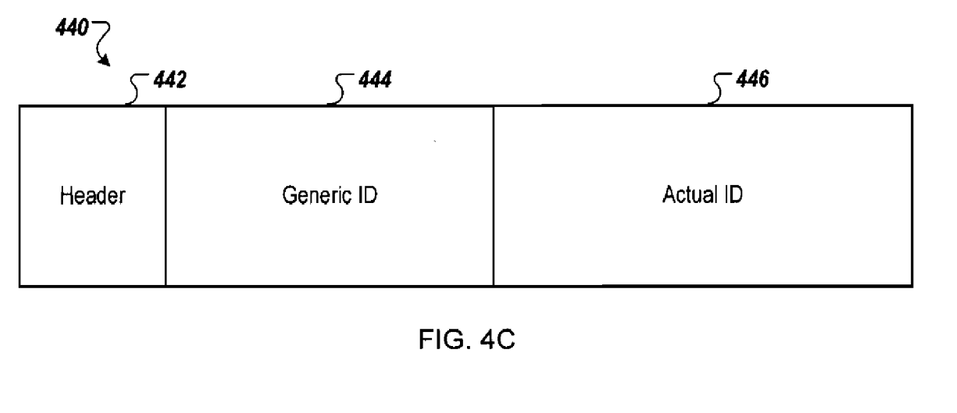

FIG. 4C depicts an example data packet 440. The data packet 440 is sent from the pharmacy system 102 to the transaction system 122. The data packet 440 is created and/or processed by the interface module 106, and transmitted over the network 108. The data packet 440 is received and/or processed by the interface module 124. The data packet 440 includes a header section 442, similar or identical to the header section 402. The data packet 440 includes a generic ID section 444, similar or identical to the generic ID section 404.

The data packet 440 includes an actual ID section 446. The actual ID section includes information about the actual ID or IDs associated with the generic ID. For example, the actual ID section 446 includes a list of items and quantities associated with the actual ID. In some implementations, the actual ID itself indicates the items and quantities, or is a pointer to information stored on another system.

Information transferred between the various systems described is sent immediately or is delayed. For example, delaying or rearranging the order data packets are sent provides an extra degree of privacy by making it more difficult, if not impossible, to correlate private information. Similarly, information written to the databases and/or processed by the modules on the various systems is rearranged or delayed to prevent correlations between private and non-private information in the systems. In some implementations, the various systems discard data to prevent private information from being stored.

Although the example systems described are related to pharmacy transaction processing, it is to be understood that the same principles are used in other industries that necessitate privacy, such as the financial or legal industries, to name two examples.

Figure 5:
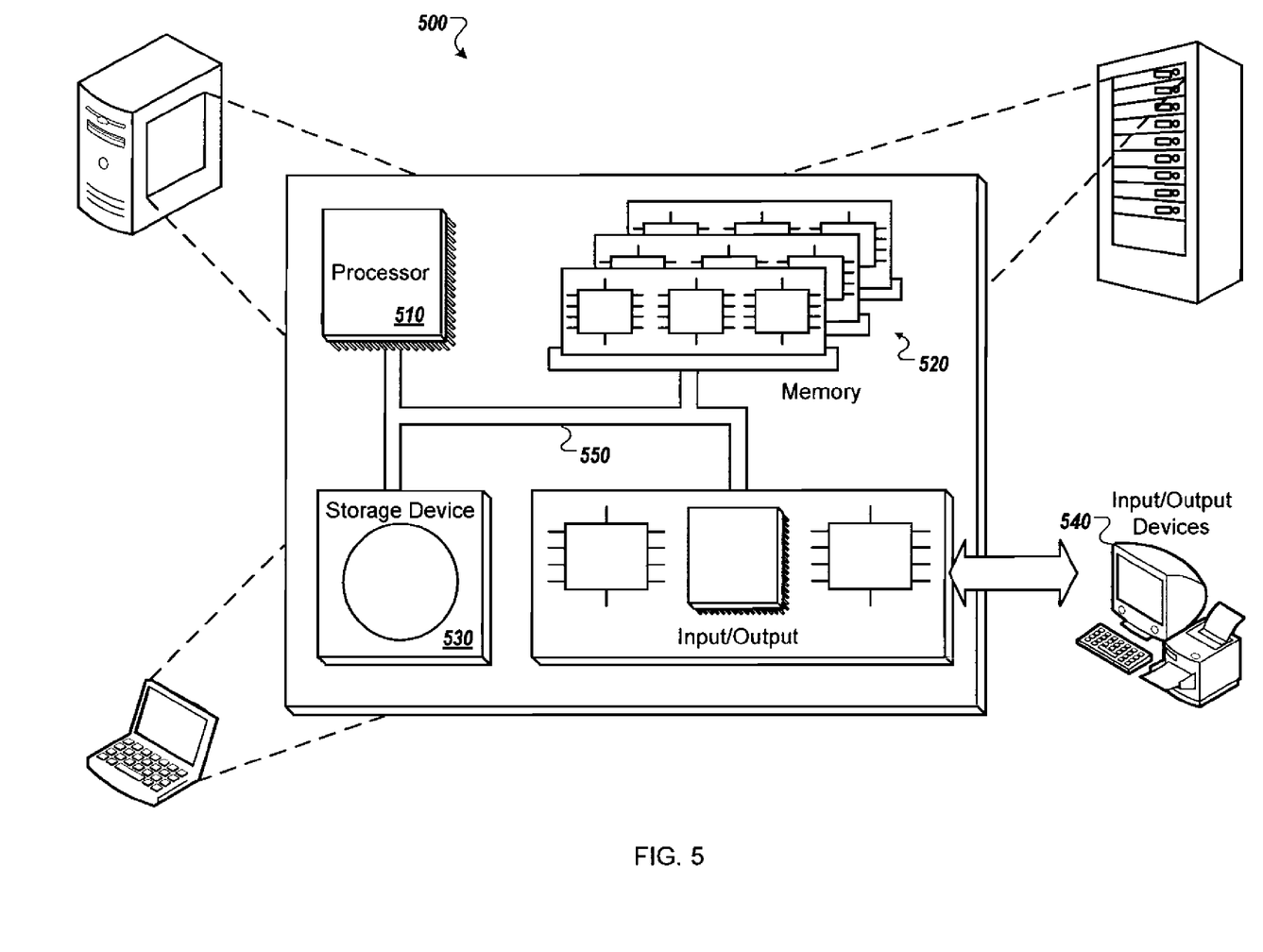
FIG. 5 is a block diagram of a computing system that can be used in connection with computer-implemented methods described in this document.

FIG. 5 is a schematic diagram of a generic computer system 500. The system 500 is used for the operations described in association with any of the computer implemented methods described previously, according to one implementation. The system 500 includes a processor 530, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 is a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks, magneto-optical disks, and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the one described. The relationship of client and server arises by virtue of computer programs running on the respective computers and having a client-server relationship to each other.

A number of embodiments have been described. Nevertheless, it will be understood that various modifications may be made without departing from the spirit and scope of this disclosure. Accordingly, other embodiments are within the scope of the following claims.

What is claimed is:

1. A method of anonymously processing pharmacy orders, the method comprising:
   generating a generic item identifier at a pharmacy computer system, the generic item identifier being associated with a pharmaceutical product without identifying the pharmaceutical product, and the generic item identifier including information to ensure that the pharmaceutical product is properly delivered;
   reading at a point of sale system the generic item identifier in connection with the processing of a transaction associated with the product;
   sending from the point of sale system a transaction record including a customer identity and the generic item identifier to the pharmacy computer system and to a transaction system;
   sending from the pharmacy computer system an updated transaction record including an actual item identifier to the transaction system, the actual item identifier identifying the pharmaceutical product;
   sending from the transaction system an inventory control record including the actual item identifier to an inventory control system; and
   modifying at the inventory control system data reflecting a stock level of the product, wherein the inventory control system does not have access to the identity of any pharmacy customer.

2. The method of claim 1, wherein the updated transaction record includes both the generic item identifier and the actual item identifier.

3. The method of claim 1, further comprising sending pharmacy sales information with the generic item identifier from the transaction system to an audit system.

4. The method of claim 2, further comprising executing an audit of the pharmacy sales data without accessing data sufficient to associate a customer with the actual item identifier.

5. The method of claim 1, wherein the transaction system reconciles actual item identifiers with generic item identifiers.

6. A system for processing pharmacy orders comprising:
   a pharmacy system to track fulfillment of orders by customers of medical products and to generate generic item identifiers associated with the medical products without identifying the medical products, the generic identifier including information to ensure that the medical products are properly delivered;
   a point of sale system to manage purchase transactions for the medical products, to read the generic item identifiers, to send purchase confirmations including the generic item identifiers to the pharmacy system, and to send transaction records with the generic item identifiers to a transaction system, wherein the point of sale system has access to information sufficient to identify the customers but not their associated medical products;
   an inventory system to receive from the transaction system inventory control messages comprising actual item identifiers, wherein the inventory system has access to information sufficient to identify the medical products but not the customers who purchased the medical products; and
   an audit system to receive from the transaction system an auditable record comprising the generic item identifier, wherein the audit system has access to information sufficient to identify the customers but not their associated medical products.

7. The system of claim 6, wherein in response to the inventory control message data reflecting in-stock quantities of the medical products is modified to reflect one or more purchase transactions.

8. The system of claim 6, wherein the transaction system receives from the pharmacy system a record comprising the actual item identifier together with other information sufficient to reconcile the actual item identifier with associated transaction.

9. The system of claim 6, wherein the pharmacy system generates messages that comprise both the generic item identifier and actual item identifier.

10. The system of claim 9, wherein the pharmacy system includes a generic ID generator and an ID management module.

11. The system of claim 6, wherein the transaction system segregates records that comprise actual item identifiers from records for the same transaction that comprise generic item identifiers or customer identity information.

12. The system of claim 11, wherein the transaction system includes a transaction management module and an ID management module.

13. A method of clearing pharmacy transactions, the method comprising:
- providing to a customer a medical product bearing a machine readable identifier at a prescription system, wherein the medical product cannot be readily identified without access to other data securely stored at the prescription system;
- reading, with a reading device, the machine readable identifier and completing a purchase of the medical product at a retail register system;
- transmitting a confirmation of the sale including data encoded in the identifier from the retail register system to the prescription system;
- transmitting sales information including data encoded in the identifier from the retail register system to an transaction management system;
- transmitting from the prescription system a record comprising an actual product key linked to the medical product, the record further comprising other data sufficient to reconcile the actual product key to the identifier; and
- modifying an inventory record to reflect a sale of the medical product, wherein such modification is executed without accessing data reflecting the identify of the customer who purchased the medical product.

14. The method of claim 13, further comprising executing an audit of the transaction based on data transmitted from the transaction management system, said data not including data sufficient to identify the customer who purchased the medical product.

15. The method of claim 13, wherein the prescription system prints a label bearing an image that encodes the identifier.

16. The method of claim 13, wherein the transaction management system associates the product key with the identifier.

17. The method of claim 13, wherein the prescription system generates a message that includes both the product key and the identifier.

18. The method of claim 13, wherein the transaction management system segregates the product key from the identifier such that they are not reconciled within the transaction management system.

19. The method of claim 13, wherein the prescription system transmits to the transaction management system a message comprising the product key and a transaction code.

20. The method of claim 19, wherein the transaction management system reconciles the product key to the transaction using the transaction code.

* * * * *